(12) United States Patent
Cima et al.

(10) Patent No.: US 12,733,995 B2
(45) Date of Patent: Sep. 15, 2026

(54) MEDICAL PROBES

(71) Applicant: Massachusetts Institute of Technology, Cambridge, MA (US)

(72) Inventors: Michael J. Cima, Winchester, MA (US); Khalil Basil Ramadi, Brookline, MA (US); Erin Byrne Rousseau, Clifton, NY (US); Max Joseph Cotler, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 19/324,979

(22) Filed: Sep. 10, 2025

(65) Prior Publication Data

US 2026/0007478 A1 Jan. 8, 2026

Related U.S. Application Data

(62) Division of application No. 17/986,647, filed on Nov. 14, 2022, now Pat. No. 12,433,685, which is a (Continued)

(51) Int. Cl.
*A61B 34/20* (2016.01)
*A61B 17/34* (2006.01)
(Continued)

(52) U.S. Cl.
CPC .......... *A61B 34/20* (2016.02); *A61B 17/3403* (2013.01); *A61B 17/3417* (2013.01); (Continued)

(58) Field of Classification Search
CPC ... A61B 34/20; A61B 2034/107; A61B 90/10; A61B 17/3403; A61B 17/3417; (Continued)

(56) References Cited

U.S. PATENT DOCUMENTS 5,938,635 A 8/1999 Kuhle
7,662,128 B2 2/2010 Salcudean et al.
(Continued)

FOREIGN PATENT DOCUMENTS

EP 1738790 A1 1/2007
JP 2006204540 A 8/2006

OTHER PUBLICATIONS

Ramezanpour et al., “Effects of Rotational Motion in Robotic Needle Insertion,” Journal of Biomedical Physics and Engineering, 2015; 5(4):207-216.
(Continued)

*Primary Examiner* — Chao Sheng
(74) *Attorney, Agent, or Firm* — Eversheds Sutherland (US) LLP

(57) ABSTRACT

A medical probe for guided insertion into soft tissue, such as the brain, is disclosed. The medical probe may include a flexible, elongated body having a proximal end portion and an opposed distal end portion. The elongated body has a length of at least 1 cm and an outer diameter of 80 μm or less. The distal end portion may comprise a beveled tip such that the distal end portion of the medical probe can be steered independently to a target site in the soft tissue.

17 Claims, 8 Drawing Sheets

Related U.S. Application Data division of application No. 16/165,583, filed on Oct. 19, 2018, now abandoned.

(60) Provisional application No. 62/574,821, filed on Oct. 20, 2017.

(51) Int. Cl.

| | |
|---|---|
| ***A61B 90/10*** | (2016.01) |
| ***A61M 5/158*** | (2006.01) |
| *A61B 34/10* | (2016.01) |
| *A61M 25/00* | (2006.01) |

(52) U.S. Cl.

CPC ............. *A61B 90/10* (2016.02); *A61M 5/158* (2013.01); *A61B 2017/3454* (2013.01); *A61B 2034/107* (2016.02); *A61M 2025/0042* (2013.01)

(58) Field of Classification Search

CPC .......... A61B 2017/3417; A61M 5/158; A61M 2025/0042

See application file for complete search history.

(56) References Cited

U.S. PATENT DOCUMENTS

| | | | | |
|---|---|---|---|---|
| 7,822,458 | B2 | 10/2010 | Webster, III et al. | |
| 8,348,861 | B2 | 1/2013 | Glozman et al. | |
| 9,398,841 | B2 | 7/2016 | Rodriguez Y Baena et al. | |
| 2003/0057347 | A1 | 3/2003 | Weiss | |
| 2007/0016067 | A1 | 1/2007 | Webster, III et al. | |
| 2009/0149867 | A1* | 6/2009 | Glozman | A61B 34/70 600/407 |
| 2014/0276586 | A1 | 9/2014 | Swaney et al. | |
| 2016/0367272 | A1 | 12/2016 | Garrison et al. | |
| 2018/0264191 | A1 | 9/2018 | Dagdeviren et al. | |

OTHER PUBLICATIONS

Webster et al., "Design Considerations for Robotic Needle Steering," Proceedings of the 2005 Institute of Electrical and Electronics Engineers International Conference on Robotics and Automation, Barcelona, mailed Apr. 2005 (7 pages).

Van De Berg et al., "Design Choices in Needle Steering—A Review," Institute of Electrical and Electronics Engineers/American Society of Mechanical Engineers Transactions on Mechatronics, Oct. 2015; vol. 20, Issue No. 5, (11 Pages).

Webster et al., "Nonholonomic Modeling of Needle Steering," The International Journal of Robotics Research, May-Jun. 2006; 25(5-6):509-525.

Majewicz et al., "Evaluation of robotic needle steering in ex vivo tissue," Proceedings of the 2010 Institute of Electrical Engineers International Conference on Robotics and Automation, mailed May 2010, pp. 2068-2073.

International Search Report and Written Opinion for PCT/US2018/056654 dated Jan. 31, 2019.

* cited by examiner

MEDICAL PROBES

CROSS-REFERENCE TO RELATED APPLICATIONS

This application is a divisional of U.S. application Ser. No. 17/986,647, filed Nov. 14, 2022, which is a divisional of U.S. application Ser. No. 16/165,583, filed Oct. 19, 2018, which claims priority to and the benefit of U.S. Provisional Application No. 62/574,821, filed Oct. 20, 2017, all of which are incorporated by reference herein.

STATEMENT REGARDING FEDERALLY SPONSORED RESEARCH OR DEVELOPMENT

This invention was made with government support under EB016101 awarded by the National Institutes of Health. The government has certain rights in the invention.

FIELD OF THE DISCLOSURE

The disclosure generally relates to medical devices and more particularly relates to a medical probe for insertion into soft tissue and methods of targeting specific sites within soft tissue for treatment or diagnosis.

BACKGROUND

The insertion of thin probes through a variety of media is important for a number of medical applications including infusion and withdrawal of fluid, as well as electrical and photo-stimulation. For example, neurological diseases have garnered increased interest in new drug delivery strategies due to the difficulty of targeting the brain through systemic drug administration (intravenous or oral). Additionally, diseases arising from specific malfunction of a brain region are ideal candidates for targeted therapy through implanted devices. For example, epilepsy affects over 4 million adults in the U.S. alone with over $40B/yr in direct costs. Parkinson's disease affects over 10 million people worldwide and generates over $25B/yr in costs. Deep brain stimulation probes have become increasingly common to treat various neurological disorders. Over 100,000 procedures have been performed, with each costing on average $50,000.

Biological implant dimensions are generally minimized to reduce trauma of insertion as well as foreign body response. In a clinical scenario, probe size is minimized to reduce trauma. For the same reason, the number insertion points are minimized. Both aspects are particularly important in the brain, where trauma needs to be minimized. However, the size minimization is limited by functional and mechanical requirements of the implant and by conventional beliefs about the insertion/deployment process of such implants into patients' soft tissues.

Microcapillaries (<100 μm) have been inserted into the brain to target specific regions. However, these conventional probes have been inserted only with the use of a larger guide tube or shuttle due to their small size and fragility, wherein the microcapillary extends merely a few millimeters out of the guide tube or shuttle. Accordingly, the large size of the shuttle obviates the benefit of the small size of the microcapillary. In addition, the small size of these probes presents a unique challenge in handling and insertion to desired targets without breakage while maintaining high precision. Such small-scale capillaries, sometimes thinner than a human hair, have been considered unsuitable for unsupported insertion due to their high aspect ratio (length: diameter) making them susceptible to buckling and breaking, limiting their applicability to uses requiring precise guided insertion. Since the high aspect ratio of such capillaries causes them to be highly flexible and prone to buckling upon insertion into tissue, the microscale probes conventionally used in neuroscience are always inserted with the help of a larger guide shuttle or a dissolvable support material. However, these relatively large auxiliary components negate the potential advantages of the microcapillaries to reduce trauma and scarring.

It therefore would be desirable to provide improved medical probes and microcapillary devices and improved methods of targeted/guided insertion of such medical probes to internal soft tissue sites (e.g., the brain) for a variety of treatment and other medical interventions.

SUMMARY

Some or all of the above needs and/or problems may be addressed by certain embodiments of the medical probes and methods disclosed herein. Medical probes for guided insertion into soft tissue are provided, along with methods of inserting and using those medical probes.

In one aspect, a medical probe for insertion into soft tissue is provided. The medical probe includes: a flexible, elongated body having a proximal end portion and an opposed distal end portion, wherein the elongated body has a length of at least 1 cm and an outer diameter of 80 μm or less (e.g., between 10 and 80 μm), and wherein the distal end portion comprises a beveled tip such that the distal end portion of the medical probe can be steered independently to a target site in the soft tissue. The beveled tip may have a bevel angle between about 15 degrees and 85 degrees. The elongated body may be a microcapillary and may be formed of a biocompatible glass or metal.

In another aspect, a method of inserting a medical probe into soft tissue is provided. In some embodiments, the method includes: identifying a target site in the soft tissue; providing an elongated medical probe having an outer diameter between 10 and 80 μm and comprising a distal end portion having a beveled tip; and independently steering the distal end portion of the medical probe into the soft tissue a distance, e.g., at least 1 cm, to reach the target site. In embodiments, the distal end portion of the medical probe including the beveled tip, e.g., at least 1 cm of the distal end portion, is unsupported during the steering and insertion. The soft tissue may be the brain of a patient in need of treatment and/or diagnosis. The steering may include rotating the beveled tip about a longitudinal axis of the medical probe during insertion into the soft tissue. The step of providing the medical probe may include selecting the medical probe which has a bevel angle of the beveled tip predetermined to produce a radius of curvature of insertion trajectory desired to reach the target site from an initial insertion point.

In still another aspect, a method of treatment of a specific site in soft tissue in a patient is provided. In some embodiments, the method includes: identifying a target site in the soft tissue; providing a medical probe comprising a distal end portion having a beveled tip, wherein providing the medical probe comprises selecting the medical probe which has a bevel angle of the beveled tip predetermined to produce a radius of curvature of insertion trajectory desired to reach the target site from an initial insertion point; independently steering the distal end portion of the medical probe into the soft tissue a distance, e.g., of at least 1 cm, to reach the target site; and then delivering a treatment substance or energy through the medical probe and out of the distal end portion to the target site in the soft tissue. The soft tissue may be the brain of a patient in need of treatment. In some embodiments, the medical probe is a microcapillary and a pharmaceutically active agent is delivered through a lumen of the microcapillary to the target site. In some other embodiments, the medical probe is solid and electrical and photo-stimulation is delivered through the probe to the target site.

In yet another aspect, a method of diagnosis of a patient is provided. In some embodiments, the method includes: identifying a target site in a soft tissue in the patient; providing a medical probe comprising a distal end portion having a beveled tip, wherein providing the medical probe comprises selecting the medical probe which has a bevel angle of the beveled tip predetermined to produce a radius of curvature of insertion trajectory desired to reach the target site from an initial insertion point in the patient; independently steering the distal end portion of the medical probe into the soft tissue a distance of at least 1 cm to reach the target site; and withdrawing a fluid sample from the target site through a lumen in the medical probe and then analyzing the fluid sample.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

FIG. 4A is taken from an optical image, and FIGS. 4B and 4C are taken from fluorescent images taken during testing.

DETAILED DESCRIPTION

Figures 1, 2:
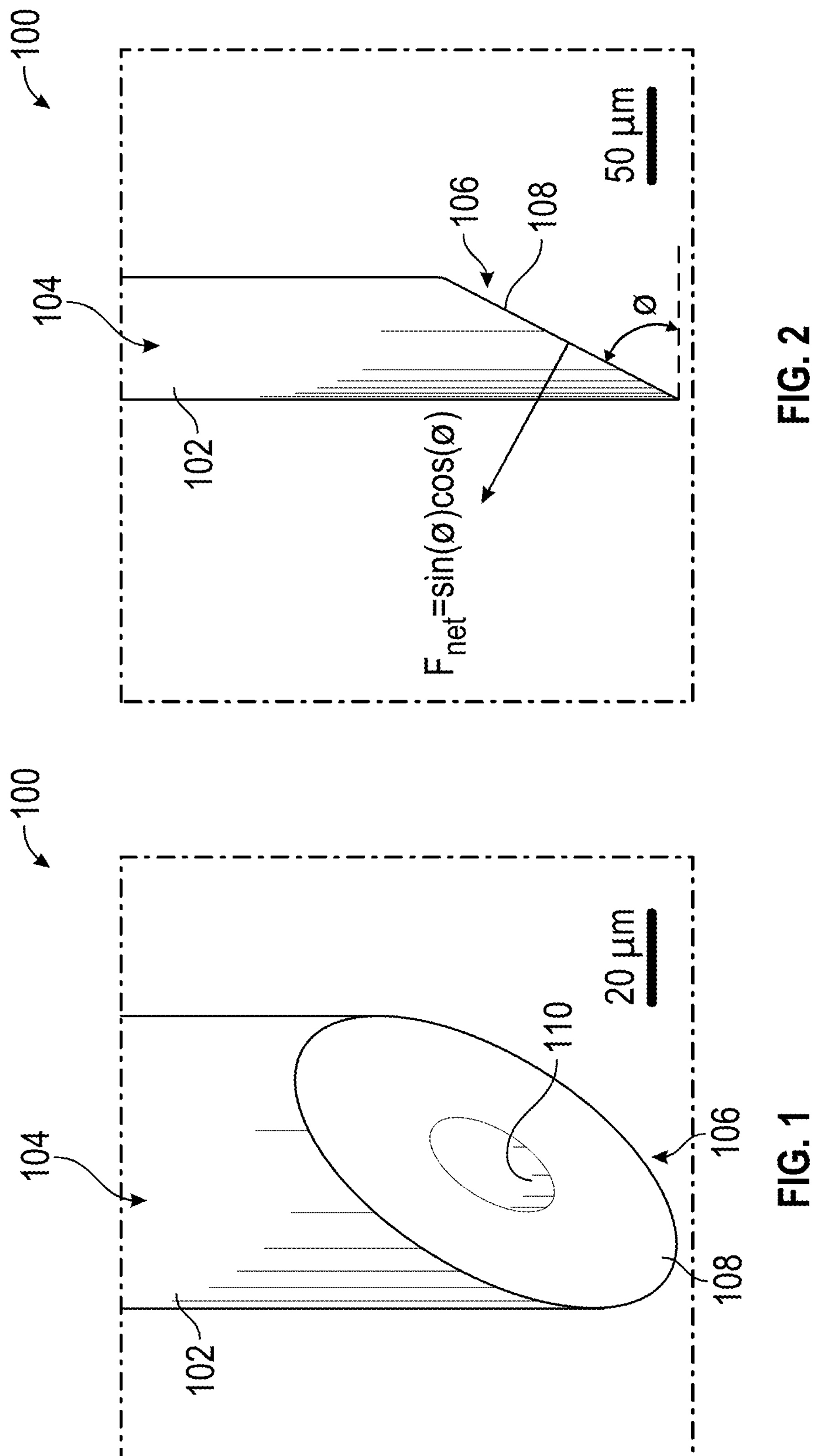
FIG. 1 is a perspective view of a beveled tip end of a capillary medical probe in accordance with one or more embodiments of the disclosure. The line drawing of this figure is a reproduction for clarity of a scanning electron microscopy (SEM) image of a bevel tipped borosilicate capillary that was produced.
FIG. 2 is a side view of a beveled tip end of a medical probe, depicting a beveled tip having an angle θ and a theoretical force F, in accordance with one or more embodiments of the disclosure. The line drawing of this figure is a reproduction for clarity of an SEM image of a bevel tipped borosilicate capillary that was produced.

Improved medical probes for insertion into soft tissue have been developed and are disclosed herein. In certain embodiments, the probe is a microscale, flexible elongate structure having a large aspect ratio, yet advantageously can be inserted into and steered in the soft tissue without the use of real-time imaging guidance and without the use a larger guide tube or shuttle to accurately and reproducibly reach a target site (e.g., an anatomical structure) in the tissue.

It has been surprisingly discovered that-unlike larger diameter probes-probes having an outer diameter of 80 microns, 60 microns, or less, are small enough that the lateral forces produced by a beveled tip are large enough to produce a curved insertion trajectory of the probe. That is, at this small size, a defined relationship between bevel angle and trajectory curvature exists and is reproducible. It also has been surprisingly discovered that these medical probes can be inserted into soft tissue unsupported and independently, e.g., without a guide tube, without breakage of the probe.

An additional benefit of the small-scale of these medical probes is that this size range greatly reduces glial scarring when inserted into the brain as compared to conventional, larger diameter medical probes.

The Medical Probe

The medical probe generally includes a flexible, elongated body having a proximal end portion and an opposed distal end portion, wherein the elongated body has a length of at least 1 cm and an outer diameter of 80 μm or less, and wherein the distal end portion comprises a beveled tip such that the distal end portion of the medical probe can be steered independently to a target site in the soft tissue. As used herein, the term "independently steering" means without mechanical support of at least 1 cm of the distal end portion of the probe and without the use of real-time imaging guidance.

As detailed in the examples, the geometry of at least the distal portion of the medical probe are important to produce the asymmetric force and deflection needed for non-linear steering of the probe in biological tissue. In preferred embodiments, the elongated body is cylindrical in shape, i.e., it has a circular cross-sectional shape when viewed along the longitudinal axis extending between the proximal and distal ends. In some embodiments, the outer diameter of the elongated body of the probe is from 5 μm to 80 μm, e.g., from 10 μm to 80 μm, 20 μm to 80 μm, from 25 μm to 80 μm, from 30 μm to 80 μm, or between 30 and 80 μm. In some embodiments, the outer diameter of the elongated body of the probe is from 5 μm to 60 μm, e.g., from 10 μm to 60 μm, 20 μm to 60 μm, from 25 μm to 60 μm, from 30 μm to 60 μm, or between 30 and 60 μm. In some embodiments, the outer diameter of the elongated body of the probe is from 40 μm to 80 μm, e.g., from 50 μm to 80 μm, from 60 μm to 80 μm, or between 60 and 80 μm. It is possible that other diameters of the elongated body may be used in some embodiments.

The angle of the beveled tip correlates to the radius of curvature of the insertion path of the medical probe in biological tissue. A bevel angle is defined by the intersection between a longitudinal axis of the body and the beveled tip surface. In some embodiments, the beveled tip has a bevel angle from about 15° to about 85°, from about 30° to about 70°, from about 25° to about 60°, or from about 35° to about 45°. In some embodiments, the beveled tip has a bevel angle between about 30 degrees and 80 degrees. The angle may be selected based on the preferred radius of curvature identified to reach a selected target tissue site from a selected initial point of insertion into the tissue. The beveled tip surface preferably is substantially planar.

The medical probe may have essentially any length suitable for use. Typically, the length is at least 1 cm. In some embodiments, the elongated body has a length from 1 cm to 20 cm. In some embodiments, at least 1 cm, or at least 2 cm, of the distal end portion including the beveled tip is unsupported, at least during insertion to the target tissue site.

The elongated body may be formed of essentially any biocompatible material which is manufacturable in the required dimensions and possesses the desired flexibility and mechanical strength for use without breaking. In particular embodiments, the biocompatible material is a glass or metal known in the art. In some embodiments, the elongated body is formed of a borosilicate.

The elongated body of the medical probe may be a microcapillary (i.e., includes a lumen extending between the proximal and distal ends) or may be solid (i.e., includes no lumen extending between the proximal and distal ends). In some preferred embodiments, the elongated body of the microcapillary is annular in shape. The description of microcapillaries in the examples below also applies to solid medical probes except where the lumen is essential (e.g., for the transport of substances therethrough).

In some embodiments, the medical probe has an elongated body having a length from 1 cm to 20 cm and an outer diameter between 30 and 80 μm, and the beveled tip has a bevel angle between about 15° and 85°, e.g., from 30° to 80°. In some of these embodiments, the outer diameter is between 30 μm and 60 μm, or between 40 μm and 75 μm. In some of these embodiments, the elongated body has a proximal end portion and a distal end portion which comprises the beveled tip, and at least 1 cm of the distal end portion including the beveled tip is unsupported. The proximal end of the elongated body may be configured for attachment to (i) a fluid transfer device such as a pump or syringe, and/or (ii) an electrical energy source or light energy source. Such attachment may be with or adapted from conventional means for operably connecting known pumps and conventional larger medical probes. The elongated body may be a metal or glass microcapillary, such a borosilicate microcapillary.

In some embodiments, a kit is provided that includes two or more medical probes having different predefined bevel angles. That is, the angle of the bevel of the beveled tip of at least one of the medical probes is different from the angle of the bevel of the beveled tip of at least a second of the medical probes. For example, a kit may include ten or more different bevel angles (e.g., 20°, 25°, 30°, 35°, 40°, 50°, 55°, 60°, 65°, 70°), such that a physician can select the appropriate one after determining a desired radius of curvature for a particular insertion path to reach a target tissue site in a patient.

FIG. 1 illustrates the distal end portion of one embodiment of medical probe 100. The medical probe 100 includes a flexible, elongated body 102 having a proximal end portion 104 and an opposed distal end portion 106. The distal end portion 106 has a beveled tip 108. The medical probe 100 is a microcapillary, and the elongated body 102 includes a lumen 110 extending between the ends, e.g., through the longitudinal axis of the medical probe. FIG. 2 shows the angle θ of the bevel of the beveled tip 108 of the medical probe 100, and the net force $F_{net}$ as it related to the bevel angle.

Insertion Systems

Systems also are provided for guiding insertion of the medical probe into soft tissue. In embodiments, the system includes at least of the medical probes described herein, and an insertion system which is operable to steer the distal end portion of the at least one medical probe a traverse distance, e.g., at least 1 cm, into the soft tissue without the use of a guide tube or shuttle. Suitable insertion and steering mechanisms for operable engaging with the proximal end of the medical probe (or any portion between the proximal end and the distal end) may be adapted from those known in the art. For example, the insertion system may include a motor, actuator, and controller configured to linearly displace and axially rotate the at least one medical probe. For example, the proximal end portion of the medical probe may be releasably fixed to an actuator that is mechanically coupled to the motor. Micromotors and step motors are known in the art for controlling linear and rotation movements at micrometer scale distances.

Methods of Inserting the Medical Probe

Methods for guided insertion of a medical probe into soft tissue are provided. The soft tissue may be essentially any suitable biological tissue of a patient. The patient may be a human or other mammal, for example. The soft tissue may be a neural tissue, such as the brain or a nerve. In some embodiments, the soft tissue is the brain of a patient in need of treatment and/or diagnosis. In other instances, the soft tissue is one or more abdominal organs (e.g. the liver and/or lungs) of a patient in need of treatment and/or diagnosis. The soft tissue may be essentially any suitable biological tissue of a patient that has a localized disease (e.g., a tumor, abscess, etc.) in need of treatment and/or diagnosis.

In some embodiments, the method of inserting a medical probe into soft tissue includes: (i) identifying a target site in the soft tissue; and then (ii) independently steering the distal end portion of the medical probe into the soft tissue a distance to insert the beveled tip to reach the target site. The distance may be at least 1 cm, or at least 2 cm, wherein at least 1 cm, or at least 2 cm, of a distal end portion of the medical probe including the beveled tip is unsupported during the steering. The insertion path is generally non-linear, e.g., arcuate.

In some embodiments, the steering comprises rotating the beveled tip about the longitudinal axis of the elongated bodying during insertion into the soft tissue. Rotational steering can be useful for an insertion trajectory that includes two or more different radii of curvature, e.g., to steer around and avoid certain more sensitive anatomical structures. In another case, the inclusion of rotation can be useful for reaching two or more different target sites without or with only partial withdrawal of the probe, which advantageously can help minimize collateral tissue damage and scarring.

In some embodiments, the step of identifying a target site in the soft tissue comprises imaging the soft tissue and identifying an initial insertion point and an insertion trajectory desired to reach the target site from the initial insertion point. Any suitable imaging devices may be used, including CT or the like. In some embodiments, the step of providing the medical probe comprises selecting a medical probe which has a bevel angle of the beveled tip predetermined to produce a radius of curvature of insertion trajectory desired to reach the target site from the initial insertion point.

For example, a surgeon may begin by imaging the brain or other soft tissue site to be treated. Using the image data from the treatment site, the surgeon can map a pathway to the treatment site, from a specific insertion site, such as a burr hole. Through the known and predictable relationship, disclosed herein, between the bevel angle and the radius of curvature, the physician can select an appropriate beveled tip probe from a kit containing multiple probes (e.g., microcapillaries) with different bevel angles. The probe may then be directly inserted without the need for a guide tube or shuttle, including depths of 1 cm or more. Alternatively, it would be possible for a surgeon, in real-time, to polish the desired bevel angle on the probes prior to use. Due to the flexibility of the probes a second treatment site may be reached utilizing the original insertion hole, through guiding the probes to a different anatomic site by varying the rotation during insertion, or through the use of a different bevel angle on a new probe.

In this way, the insertion method allows for the control of the micron-scale probes during insertion through steering, allowing them to precisely target an anatomically diverse set of targets with no or minimal probe fracture. The method may include imaging a soft tissue area that requires treatment, such as the brain. The surgeon may then identify a targeted treatment area prior to the insertion of the probe through a burr hole into the soft tissue without the use of a guide, sheath, or shuttle. During insertion, the surgeon may then steer the tip of the probe by rotating the probe about its longitudinal axis during insertion, the resulting force causing the tip of the probe to follow a predictable arc as it is inserted.

When the probe is inserted, the resulting force causes the tip to follow a predictable arc (if inserted linearly) or corkscrew (if rotated during insertion). By rotating the probe during the insertion, precise positioning of the tip in three dimensions can be achieved allowing the device to be guided, or steered along numerous different paths to multiple different anatomical locations from a single insertion point. Various bevel angles may be utilized to achieve different radii of curvature during implantation/insertion. These configurations allow for significantly deeper unsupported insertion of capillaries in this size range than was previously assumed feasible.

With the ability to guide or steer the probe through the soft tissue during insertion, non-linear pathways can be taken to targeted treatment sites, which can allow for access to multiple anatomical locations from a single insertion point, and allow the insertion process to be guided around and away from sensitive tissues. With predictable guidance, the need for real-time imaging of the insertion process is obviated which is additionally beneficial due to the difficulty of imaging such small-scale probes. Implantation (insertion) of solid probes and microcapillaries such as the ones described here may be particularly useful for their ability to target different regions of the brain, for example, through a single burr hole, decreasing risk for surgical morbidity and mortality.

Methods of Using the Medical Probe

The medical probes disclosed herein may be used for essentially any suitable purpose. This purpose typically includes the transport of substances or energy to or from the target tissue site. The target tissue site may be in healthy soft tissue or diseased tissue, e.g., a tumor. In some embodiments, the probe is a microcapillary effective for transport of fluid substances therethrough, e.g., of the delivery of a pharmaceutical agent to the target tissue site or the withdrawal of a biological fluid at the site. In some other embodiments, the medical probe is solid or a microcapillary and is used to deliver electrical energy or light to stimulate certain cells or nerves at the tissue site, or to sense electrical signals.

In some embodiments, a method is provided for treatment of a specific site in soft tissue in a patient. The method includes (i) identifying a target site in the soft tissue; (ii) independently steering the distal end portion of the medical probe into the soft tissue a distance to insert the beveled tip to reach the target site; and then (iii) delivering a treatment substance or energy through the elongated body of the medical probe and out of the distal end portion to the target site in the soft tissue. The step of identifying a target site in the soft tissue may include imaging the soft tissue and identifying an initial insertion point and an insertion trajectory desired to reach the target site from the initial insertion point. The step of steering the distal end of the medical probe may include inserting the tip a distance of at least 1 cm, or at least 2 cm, wherein the distal end portion of the probe is unsupported. In some embodiments, the soft tissue is the brain of the patient. In some particular embodiments, the medical probe is a microcapillary, the soft tissue is the brain, and a pharmaceutically active agent is delivered through a lumen of the microcapillary to the target site.

In some particular embodiments, the treatment method includes (i) identifying a target site in the soft tissue; (ii) providing a medical probe comprising a distal end portion having a beveled tip, wherein providing the medical probe comprises selecting the medical probe which has a bevel angle of the beveled tip predetermined to produce a radius of curvature of insertion trajectory desired to reach the target site from an initial insertion point; (iii) independently steering the distal end portion of the medical probe into the soft tissue a distance to reach the target site; and (iv) delivering a treatment substance or energy through the medical probe and out of the distal end portion to the target site in the soft tissue. The step of identifying a target site in the soft tissue may include imaging the soft tissue and identifying the initial insertion point and the insertion trajectory desired to reach the target site from the initial insertion point. The step of steering the distal end of the medical probe may include inserting the tip a distance of at least 1 cm, wherein the distal end portion of the probe is unsupported.

In some embodiments, the medical probe is a microcapillary used to deliver drugs, of specific volumes and administration timelines, to targeted regions of the body. In some particular embodiments of the method, the medical probe is a microcapillary, the soft tissue is the brain, and a drug is delivered through a lumen of the microcapillary to the target site. The drug may be essentially any prophylactic or therapeutic agents, or any active pharmaceutical ingredient, known in the art. The drug typically is in liquid excipient vehicle, such as water or saline. The drug may include a neuromodulating agent. In some embodiments, the neuromodulating agent comprises muscimol or another GABA agonist. Other neuromodulating agents known in the art also may be used.

In some other particular embodiments, the medical probe includes a solid tubular body (e.g., borosilicate) configured for use in electrical and photo-stimulation, as known in the art.

In some embodiments, the medical probe is a microcapillary used to take liquid biopsies from the body of a patient, which may be used to identify disease type, state, and progression.

Once the medical probe is inserted at the desired location in vivo, for example, in the brain of a patient, the small size of the probes minimizes glial scarring, allowing for long-term fluid infusion and withdrawal for a variety of therapeutic and diagnostic applications.

EXAMPLES

Figure 3:
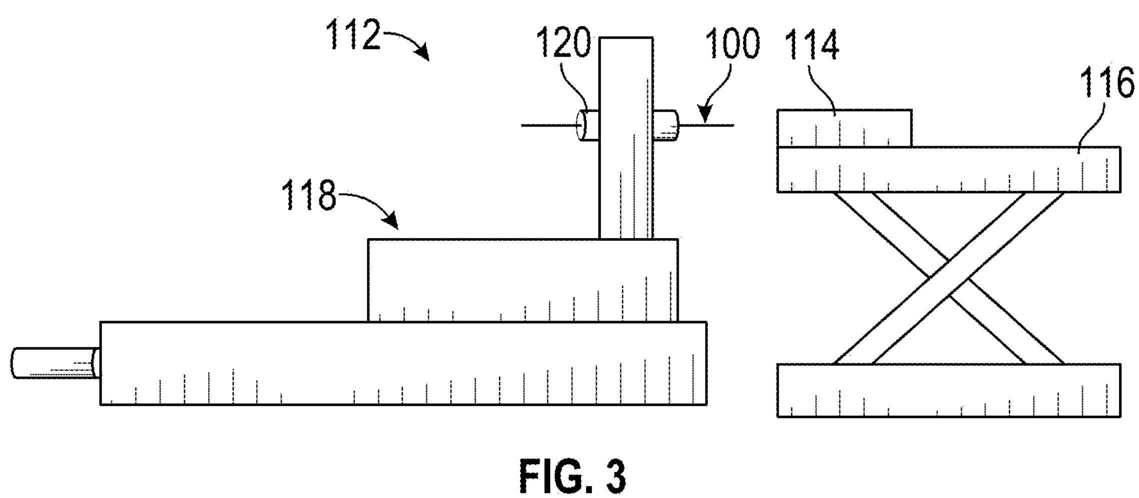
FIG. 3 depicts an experimental set-up of a linear insertion system for inserting and steering a medical probe into a soft tissue model, in accordance with an embodiment of the disclosure.
Figure 4A:
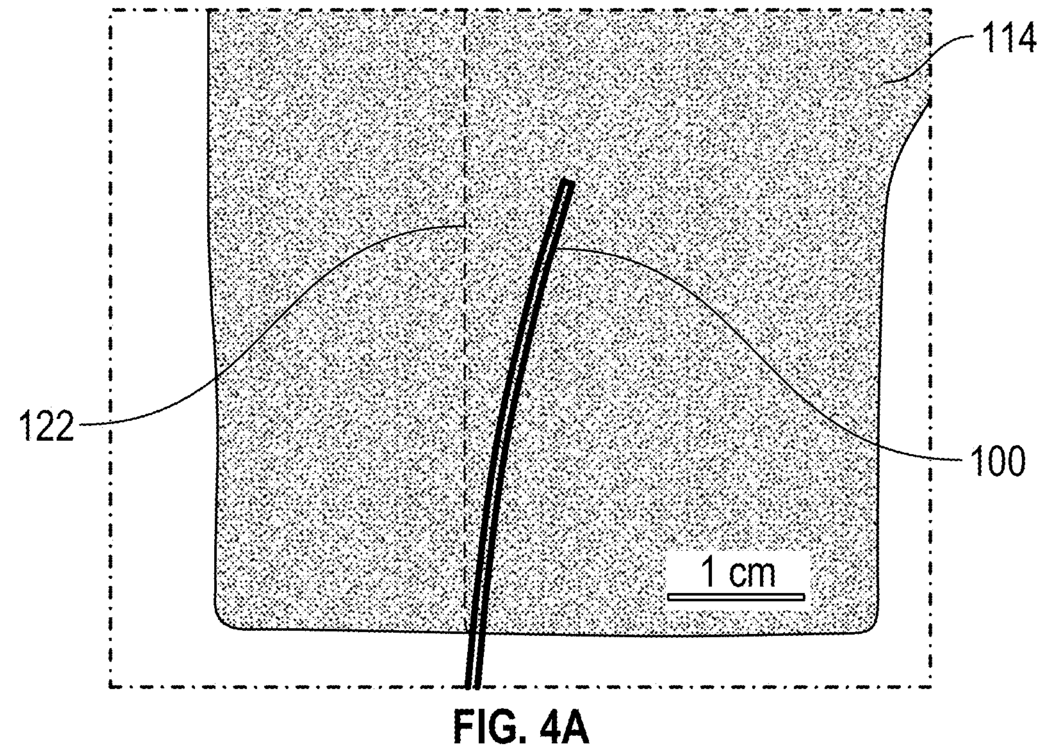
FIGS. 4A-4C depict curved trajectories of a medical probe inserted into a soft tissue model, relative to a linear insertion axis, in accordance with one or more embodiments of the disclosure. The line drawings of these figures are reproductions for clarity of photographic images of a bevel tipped borosilicate capillary that was inserted into an agarose gel tissue model.
Figure 4B:
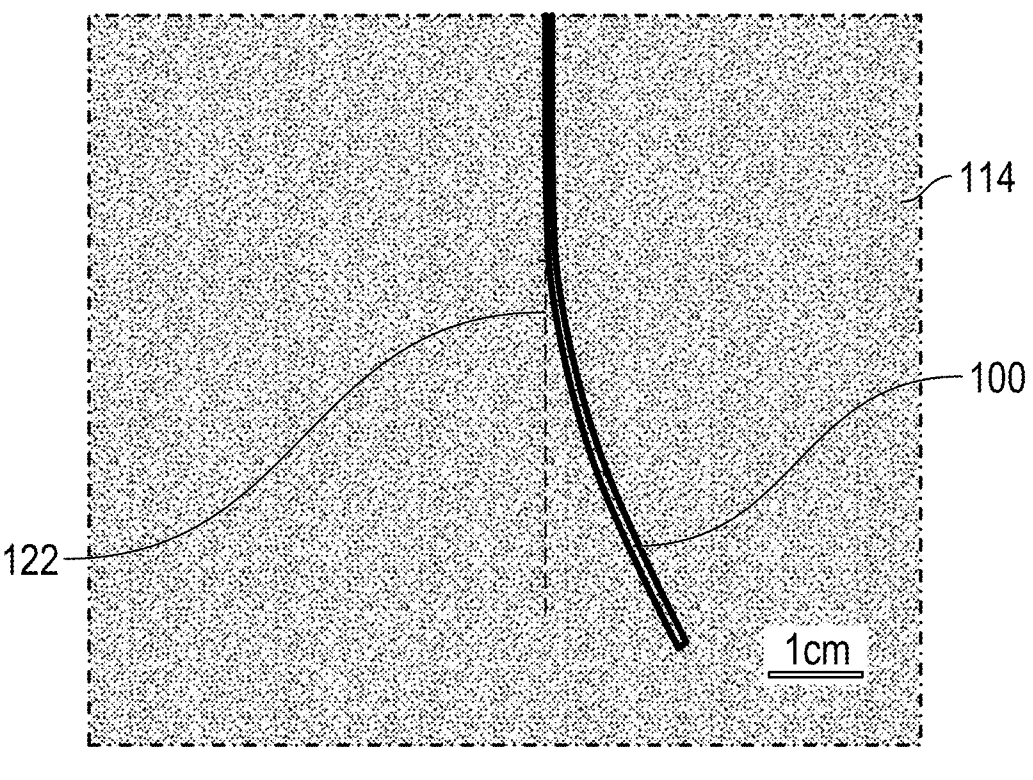
Figure 4C:
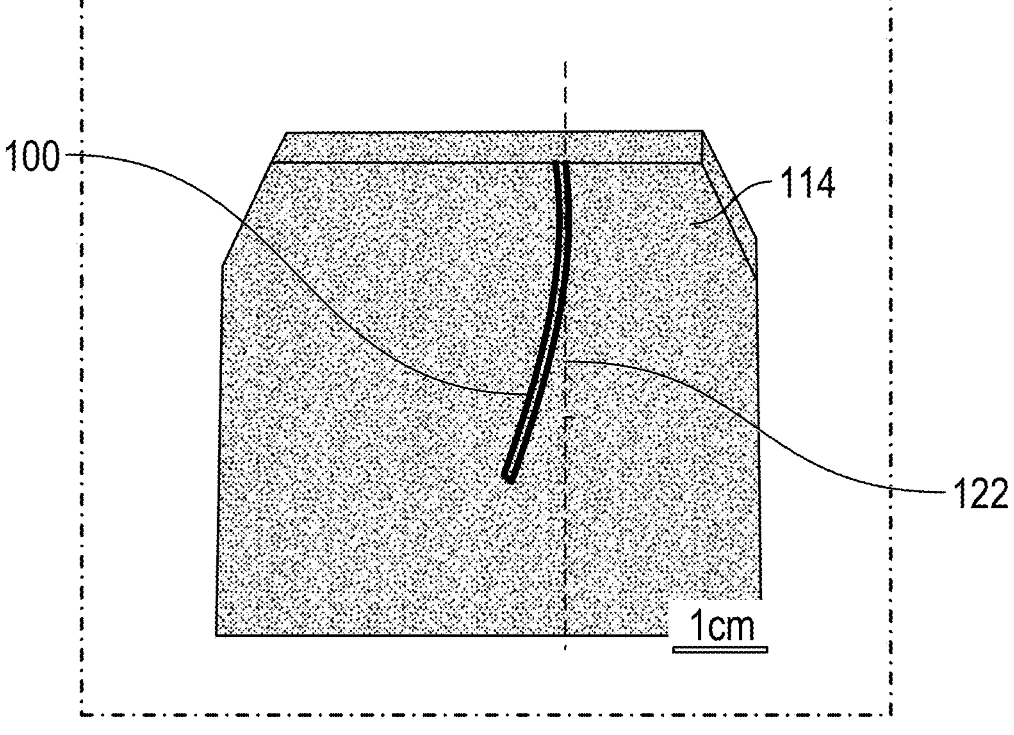

As depicted in FIG. 3, a linear insertion system 112 was used to insert and steer the medical probe 100 into a soft tissue model 114. The experimental setup depicted in FIG. 3 was used to linearly insert fibers (i.e., medical probes 100 comprising 60 micron or 80 micron OD microcapillaries having a 50° beveled tip made by polishing) into the soft tissue model 114, which in this experiment comprises 0.6% agarose gel, to curved trajectories of up to 10 cm depth. The soft tissue model 114 was disposed on an adjustable table 116, and the medical probe 100 was attached to a linear stage 118 via a fiber holder 120. The fiber holder 120 was rotatable. As can be seen in FIGS. 4A-4C, the medical probe 100 includes curved trajectories of up to 10 cm depth in the soft tissue model 114 relative to the linear insertion axis 122. The test was repeated in different insertion media.

A beveled-tip cylindrical probe experienced a net lateral force during insertion into a medium resulting in a predictable curved trajectory. This force arises from the asymmetry of the tip and is dependent on the tip geometry. A theoretical illustration of this net lateral force is shown in FIG. 2, which depicts an example beveled-tip with bevel angle ø and theoretical force F. By controlling rotation of the probe during lateral insertion, the probe trajectory curvature can be guided to a multitude of locations from a single insertion point and can be done so without the need for real-time imaging.

Figures 5A, 5B:
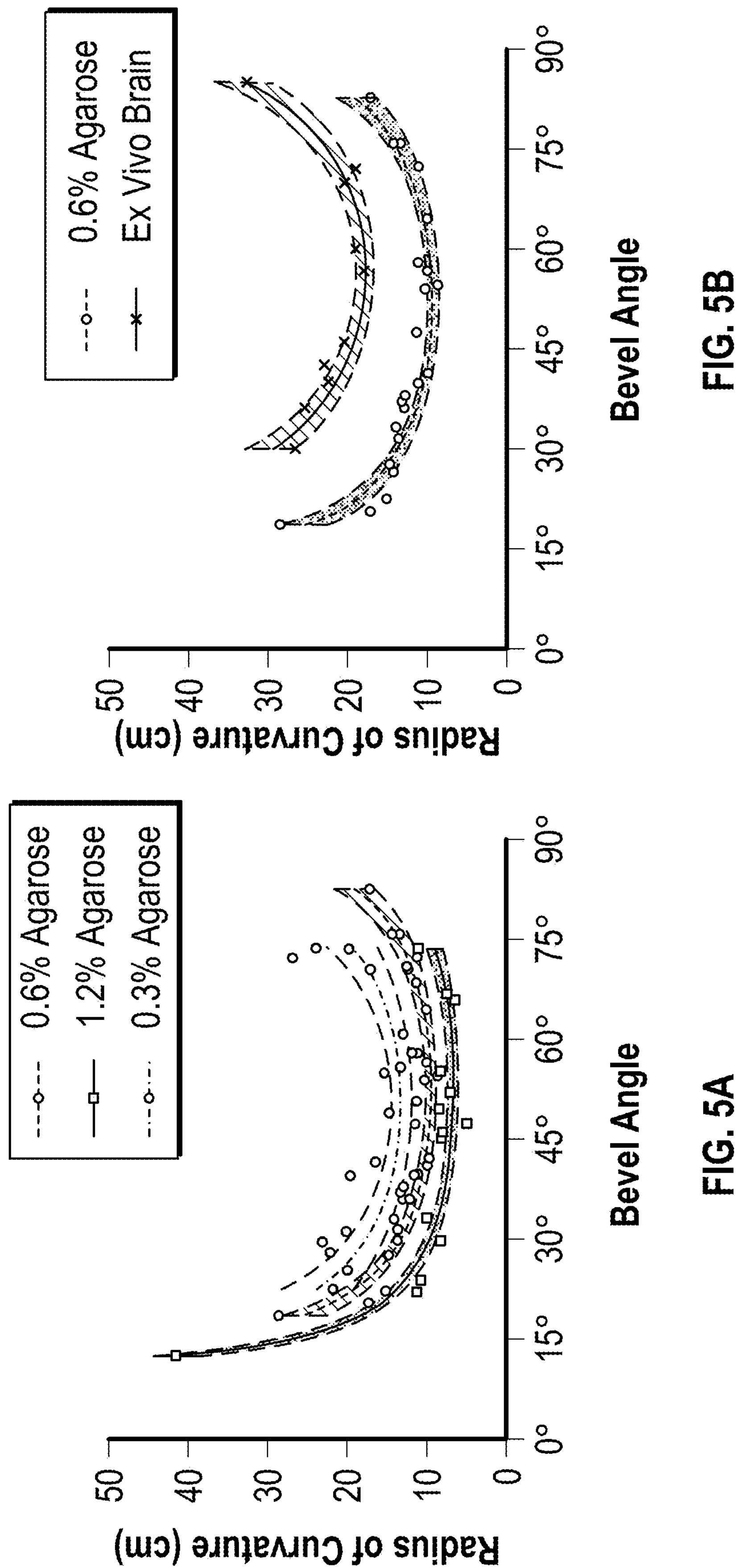
FIGS. 5A-5B are graphs depicting the radius of curvature of the insertion path (trajectory) of a medical probe inserted into different agarose tissue models and into ex vivo cow brain, as it relates to the bevel angle of the medical probe, in accordance with one or more embodiments of the disclosure.
Figure 6:
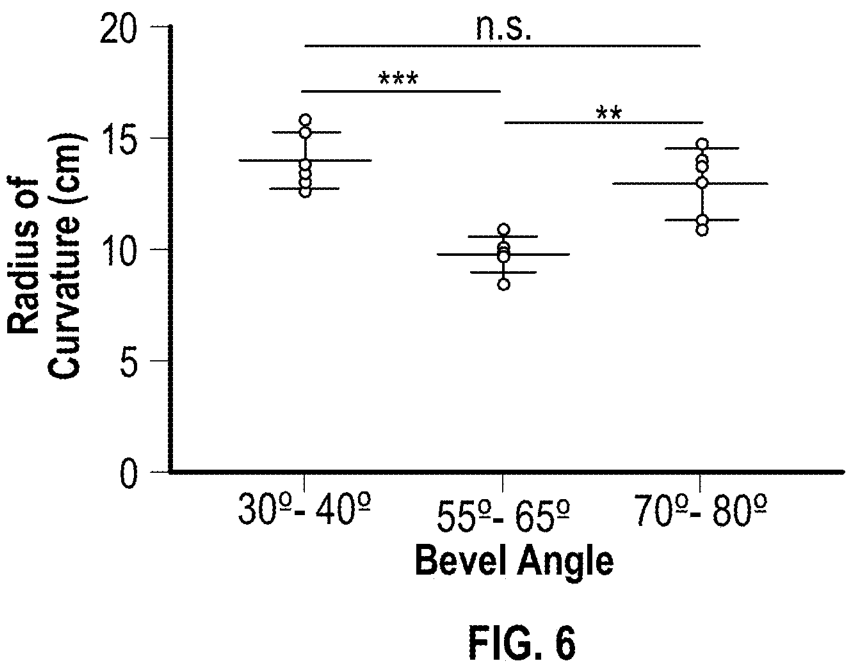
FIG. 6 is a graph which depicts the radius of curvature versus the bevel angle, in accordance with one or more embodiments of the disclosure.

As depicted in FIGS. 5A, 5B, and 6, several relationships have been identified between probe geometry and final trajectory through the systematic insertion of bevel tipped probes into 0.6% agarose gel tissue model and other media. FIGS. 5A and 5B illustrate that the radius of curvature of the 60 micron OD medical probe is predictable in multiple insertion media based upon bevel angle, while FIG. 6 illustrates that the curvature, at several bevel angles, is repeatable and statistically significant in 0.6% Agarose. For example, increased bevel angles (increased surface area) results in a lower radius of curvature (more deflection). Similar results were also obtained when repeated with 80 micron OD medical probes. This relationship can be utilized to create predicted needle trajectories for precise targeting of multiple anatomical locations in the brain or other soft tissue sites.

Figure 7A:
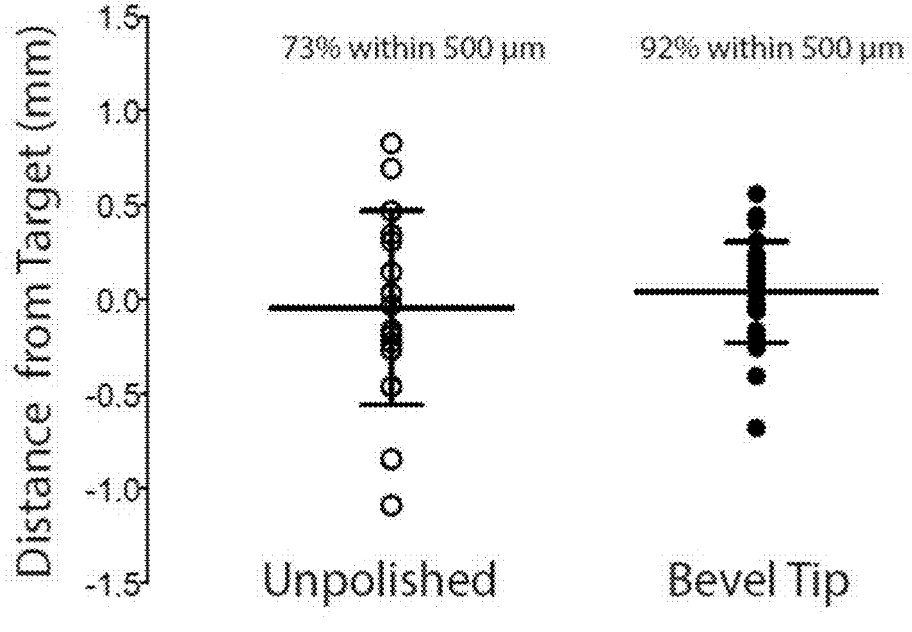
FIG. 7A is a graph which depicts insertion distance from a predetermined target for bevel tipped probes and unpolished probes in experiment assessing targeting accuracy, in accordance with one or more embodiments of the disclosure.
Figure 7B:
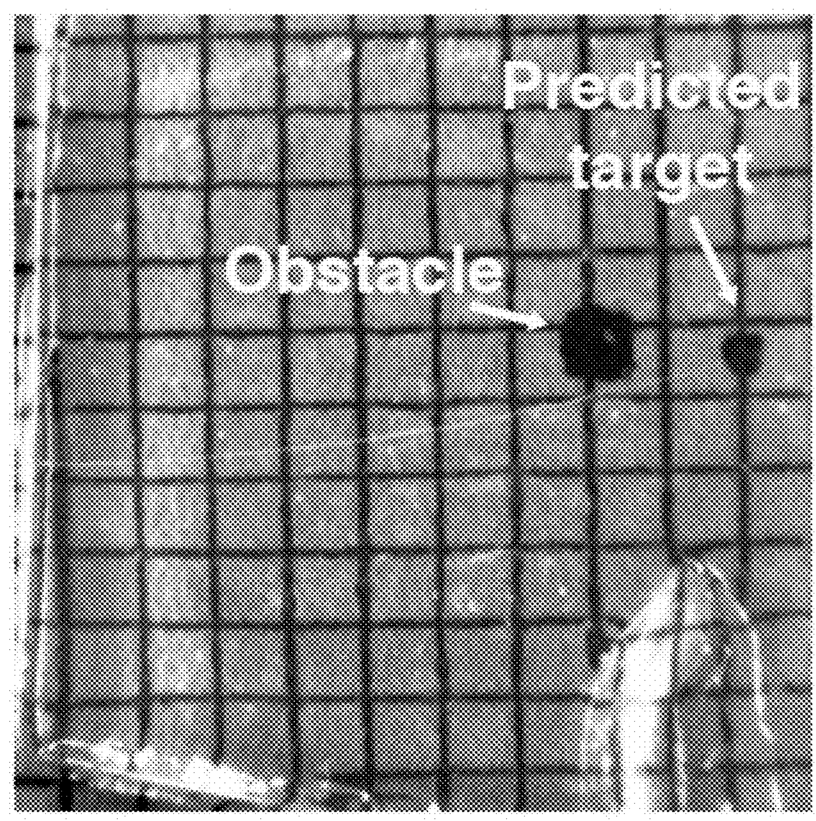
FIG. 7B is a photographic image which depicts a capillary guided within 0.5 mm of a target in 0.6% agarose gel at 2 cm while avoiding an obstacle, in accordance with one or more embodiments of the disclosure.

For a comparison of targeting accuracy, microcapillaries with no beveled tip (unpolished) were also inserted into a tissue model (0.6% agarose gel). The results, as illustrated in FIG. 7A show that the 50° bevel-tipped probes reached the target more accurately more often than the unpolished probes. FIG. 7B depicts one of these bevel-tipped probes reaching a predicted target along a curved trajectory around a hypothetical obstacle. This shows that these probes enable insertion methods which can obviate the need for any closed-loop feedback or real-time image guidance.

The tests that were conducted show that the curvature of the insertion trajectory is predictable in different insertion media based upon the bevel angle and that the curvature of the insertion trajectory is repeatable and statistically significant in the tissue models, at insertion distances of 1 cm and 2 cm.

Previous investigators have proposed using bevel angle as a means of controlling cannula deflection. However, a relationship between bevel angle and deflection has not been observed. For example, a recent publication has claimed that bevel angle had no effect on curvature ex vivo or in vivo (Van de Berg et al. *IEEE/ASME Transactions on Mechatronics*. 2015; 20 (5)) and thus, is an ineffective means for controlling or guiding the tip during insertion.

The importance of cannula dimensions to guidance has been previously unrecognized. However, a defined relationship between bevel angle and curvature in vitro and ex vivo for cannulas less than or equal to 80 microns in diameter has now been discovered. The relationship is also surprisingly reproducible, so much so, that it enables placement of cannulas in the brain without imaging guidance. In fact, the small diameter of the microcapillaries actually pronounces the effectiveness and predictability of the control.

The smallest beveled capillaries previously tested have a diameter of 500 μm. The large size of the tip limits the feasibility of using them in practice due to additional trauma. Recent publications on this have acknowledged this limitation and recommended that needle size be minimized. However, they also state that "flexible needle navigation inside the tissue is very complicated and requires implementing image processing abilities" (Ramezanpour H., Yousefi H., Rezaci M., Rostami M., *J Biomed Phys Eng* 2015; 5 (4) 211).

Here, control of flexible thin probes in tissue phantoms (models) has been achieved without image processing abilities. Although certain applications have used small-scale capillaries in the past, those applications have relied on the use of a larger guide tube or shuttle, with only a small fraction of the capillary exposed from the end of the guide tube or shuttle. As described herein, the outer diameter of the beveled capillaries may range between 10 μm and 80 μm.

Testing utilizing 60 μm and 80 μm glass fiber microcapillaries produced surprisingly repeatable results, although microcapillaries made from metals with a similar moduli of elasticity may also be suitable. Through the use of different bevel angles, different radii of curvature for the insertion path of the microcapillary can be achieved.

Figures 8A, 8B, 8C:
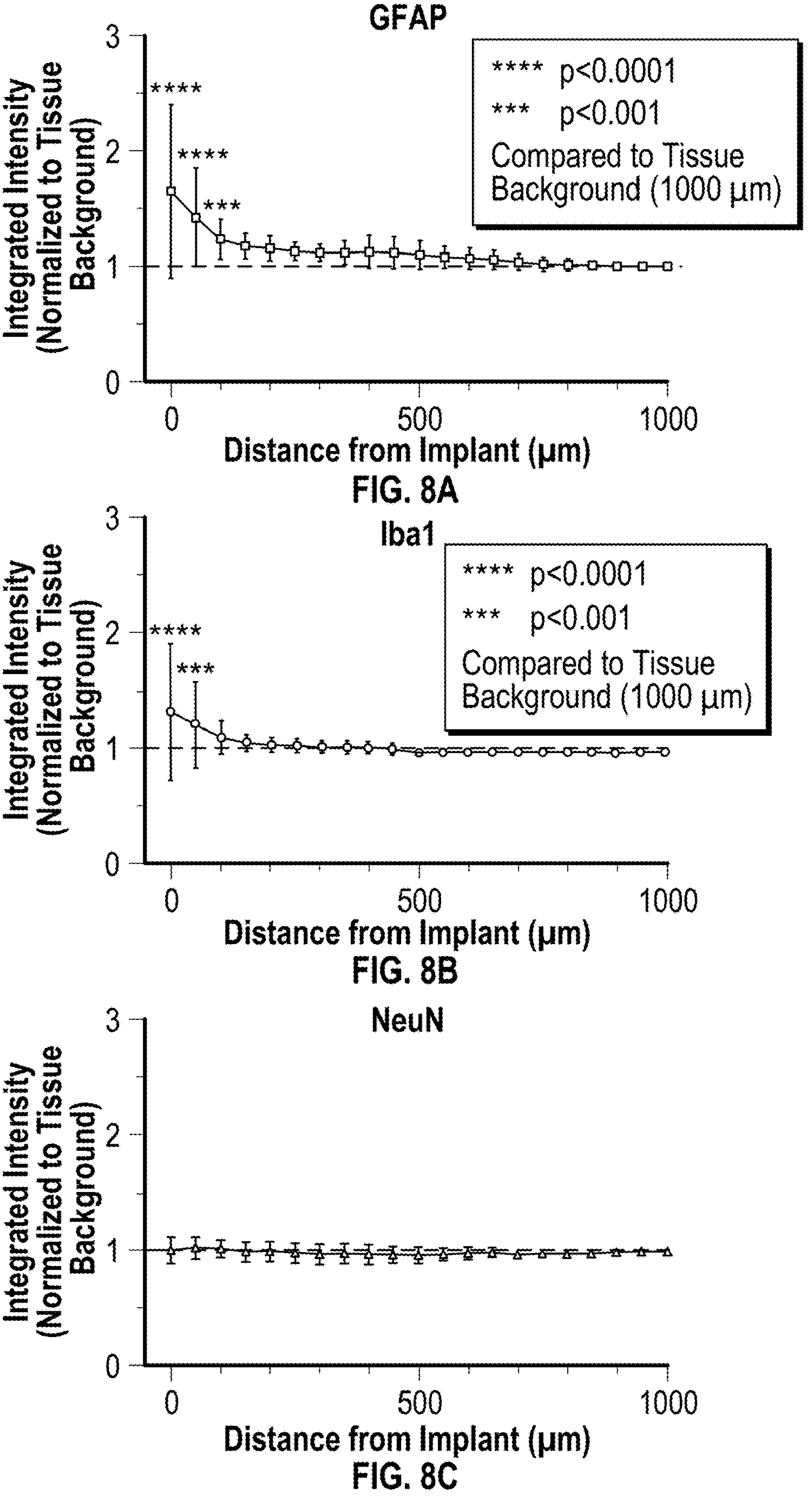
FIGS. 8A-8C are graphs depicting three biomarkers for glial scarring following 8 weeks of probe implantation in rat brain, in accordance with one or more embodiments of the disclosure.

Medical probes as described herein (60 μm diameter) were implanted in vivo in the brains of rats for eight weeks to assess tissue response to the implant (e.g., scarring). Glial fibrillary acidic protein (GFAP), neuronal nuclear protein (NeuN) antibodies, and ionized calcium-binding adapter molecule 1 (Iba1) were measured at and distal from the site of implantation as indicators for glial scarring. FIGS. 8A-8C depict the integrated intensity versus distance from implant in rats following 8 weeks of implantation. The greater the distance from the implant, the lower the integrated intensity in glial fibrillary acidic protein, ionized calcium binding adaptor molecule 1, and NeuN antibodies.

Figure 9:
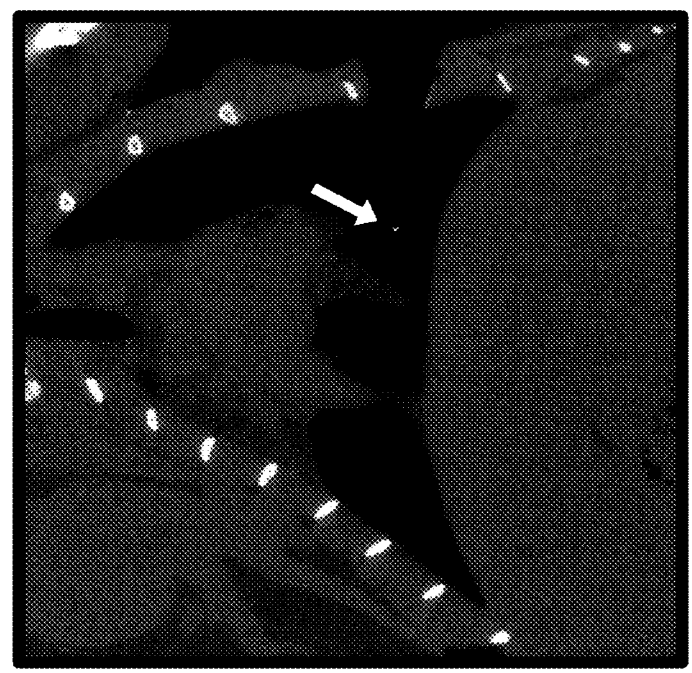
FIG. 9 shows two CT scans of 60 μm medical probes, flushed with iodine contrast agent, in rats, in accordance with one or more embodiments of the disclosure.
Figure 9:

FIG. 9 shows that the probes (microcapillaries) can be detectable in vivo when filled with a contrast agent. The arrows in FIG. 9 depict 60 μm medical probes in rat brains were detected by CT when flushed with an iodine contrast agent.

Although specific embodiments of the disclosure have been described, numerous other modifications and alternative embodiments are within the scope of the disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

We claim:

1. A medical probe for insertion into soft tissue, the medical probe comprising:

a flexible, elongated body having a proximal end portion and an opposed distal end portion, wherein the elongated body has a length of at least 1 cm and an outer diameter of 80 μm or less, wherein the distal end portion comprises a beveled tip such that the distal end portion of the medical probe can be steered independently to a target site in the soft tissue, and wherein the elongated body comprises a glass microcapillary and the beveled tip has a tip angle between 15 degrees and 85 degrees.

2. The medical probe of claim 1, wherein the outer diameter of the elongated body is between 20 μm and 80 μm.

3. The medical probe of claim 1, wherein the outer diameter of the elongated body is from 60 μm to 80 μm.

4. The medical probe of claim 1, wherein the beveled tip has a bevel angle between 30 degrees and 80 degrees.

5. A kit of parts, comprising:

two or more medical probes of claim 1, wherein the angle of the bevel of the beveled tip of at least one of the medical probes is different from the angle of the bevel of the beveled tip of at least a second of the medical probes.

6. The medical probe of claim 1, wherein the elongated body has a length from 1 cm to 20 cm.

7. The medical probe of claim 6, wherein the outer diameter of the elongated body is between 10 μm and 80 μm.

8. The medical probe of claim 1, wherein:

the outer diameter of the elongated body is between 20 and 80 μm, the beveled tip has a bevel angle between 30 degrees and 80 degrees, and the elongated body has a length from 1 cm to 20 cm.

9. A kit of parts, comprising:

two or more medical probes of claim 8, wherein the angle of the bevel of the beveled tip of at least one of the medical probes is different from the angle of the bevel of the beveled tip of at least a second of the medical probes.

10. A system for guided insertion of a medical probe into soft tissue, comprising:

at least one medical probe of claim 1; and an insertion system which is operable to steer the distal end portion of the at least one medical probe a traverse distance of at least 1 cm into the soft tissue without the use of a guide tube or shuttle.

11. The system of claim 10, wherein the insertion system includes a motor, actuator, and controller configured to linearly displace and axially rotate the at least one medical probe.

12. The system of claim 10, wherein at least 1 cm of the distal end portion of the at least one medical probe including the beveled tip is unsupported.

13. The system of claim 10, wherein at least 2 cm of the distal end portion of the medical probe including the beveled tip is unsupported.

14. The system of claim 10, wherein the bevel angle of the bevel tip is between 30 degrees and 80 degrees, and the outer diameter of the elongated body is between 20 μm and 80 μm.

15. The system of claim 10, further comprising means for identifying a target site in the soft tissue, wherein the bevel angle of the beveled tip is selected to produce a radius of curvature of insertion trajectory desired to reach the target site from an initial insertion point when the distal end portion of the at least one medical probe is independently steered into the soft tissue a distance of at least 1 cm to reach the target site.

16. The system of claim 15, wherein the combination of the outer diameter and the tip angle is selected to produce an asymmetric force on the at least one medical probe upon its linear displacement into the soft tissue to cause the distal end portion of the at least one medical probe to be independently steered to a target site in the soft tissue, wherein at least 1 cm of the distal end portion of the at least one medical probe including the beveled tip is unsupported.

17. The system of claim 16, wherein the bevel angle is between 30 degrees and 80 degrees, and the outer diameter of the elongated body is between 20 μm and 80 μm.

* * * * *